(12) United States Patent
Atkinson et al.

(10) Patent No.: US 8,512,313 B2
(45) Date of Patent: Aug. 20, 2013

(54) URINARY FLOW CONTROL VALVE WITH PRESSURE SEALING

(75) Inventors: Gordon Edgar Atkinson, Hickory, NC (US); Mitchell Wade Yadven, Bradenton, FL (US); Jeffrey Wayne Hale, Hickory, NC (US)

(73) Assignee: Advanced Urological Products, Hickory, NC (US)

( * ) Notice: Subject to any disclaimer, the term of this patent is extended or adjusted under 35 U.S.C. 154(b) by 854 days.

(21) Appl. No.: 12/611,184

(22) Filed: Nov. 3, 2009

(65) Prior Publication Data
US 2011/0106060 A1      May 5, 2011

(51) Int. Cl.
*A61M 27/00*      (2006.01)

(52) U.S. Cl.
USPC ........... 604/544; 604/328; 604/329; 604/330; 604/331; 604/274; 604/275; 604/279; 604/264; 604/276

(58) Field of Classification Search
USPC .......................................... 604/544, 264, 276
See application file for complete search history.

(56) References Cited

U.S. PATENT DOCUMENTS

| | | |
|---|---|---|
| 4,055,179 A | 10/1977 | Manschot et al. |
| 4,693,712 A | 9/1987 | Bates |
| 4,749,103 A | 6/1988 | Barriac |
| 4,934,999 A | 6/1990 | Bader |
| 4,968,294 A | 11/1990 | Salama |
| 5,114,398 A | 5/1992 | Trick et al. |
| 5,156,603 A | 10/1992 | Olsen |
| 5,234,409 A | 8/1993 | Goldberg et al. |
| 5,310,094 A | 5/1994 | Martinez et al. |
| 5,630,429 A | 5/1997 | Dann |
| 5,671,755 A | 9/1997 | Simon et al. |
| 5,988,448 A | 11/1999 | Foth |
| 6,012,181 A * | 1/2000 | Johnson et al. ............ 4/480 |
| 6,027,442 A | 2/2000 | Von Iderstein |
| 6,050,934 A | 4/2000 | Mikhail et al. |
| 6,170,720 B1 | 1/2001 | Gnepper et al. |
| 6,183,413 B1 | 2/2001 | Migachyov |
| 6,902,146 B1 | 6/2005 | Elliott |
| 6,913,244 B1 | 7/2005 | Atkinson et al. |
| 7,001,370 B2 * | 2/2006 | Kubalak et al. ............. 604/544 |
| 7,037,303 B2 | 5/2006 | Beaufore et al. |
| 2002/0133053 A1 | 9/2002 | Latour, Jr. |
| 2006/0095019 A1 | 5/2006 | Dikeman et al. |
| 2006/0137431 A1 * | 6/2006 | Fernandes et al. ............ 73/49.1 |

OTHER PUBLICATIONS

Simpla Catheter Valve; http://www.coloplast.co.uk/ECompany/GBMED/Homepage.nsf; Coloplast Ltd.; 1989.
Flip-Flo Catheter Valve; http://barduk.com/main/product.asp?sectionTypeID=2&sectionId=5&productId=239; Bard Limited; copyright 2006-2009.

* cited by examiner

*Primary Examiner* — Tatyana Zalukaeva
*Assistant Examiner* — Ilya Treyger
(74) *Attorney, Agent, or Firm* — Stevens & Showalter LLP

(57) ABSTRACT

A valve for controlling fluid flow through a flow passage. The valve includes a tubular valve body defining a longitudinal axis and having an interior surface and an exterior surface. The valve body defines first and second valve ends and a tip portion is supported on the valve body and located at the second valve end. A cap member is supported on the valve body and includes a closed end formed by an end wall having an aperture for receiving the tip portion. The aperture includes a lip portion surrounded a groove on an interior of the cap member to facilitate a pressure seal between the aperture and the tip portion.

11 Claims, 4 Drawing Sheets

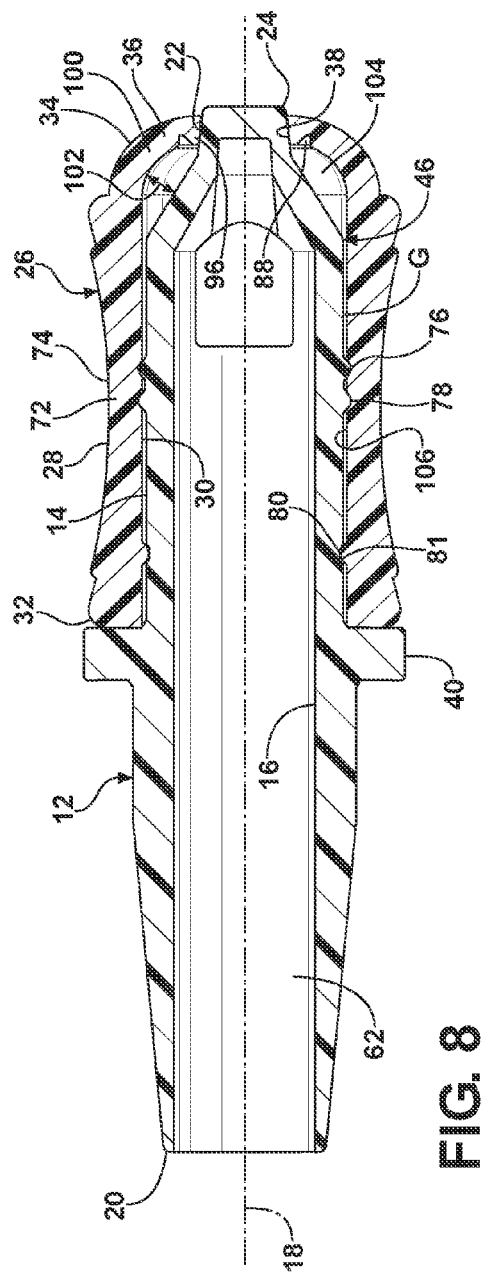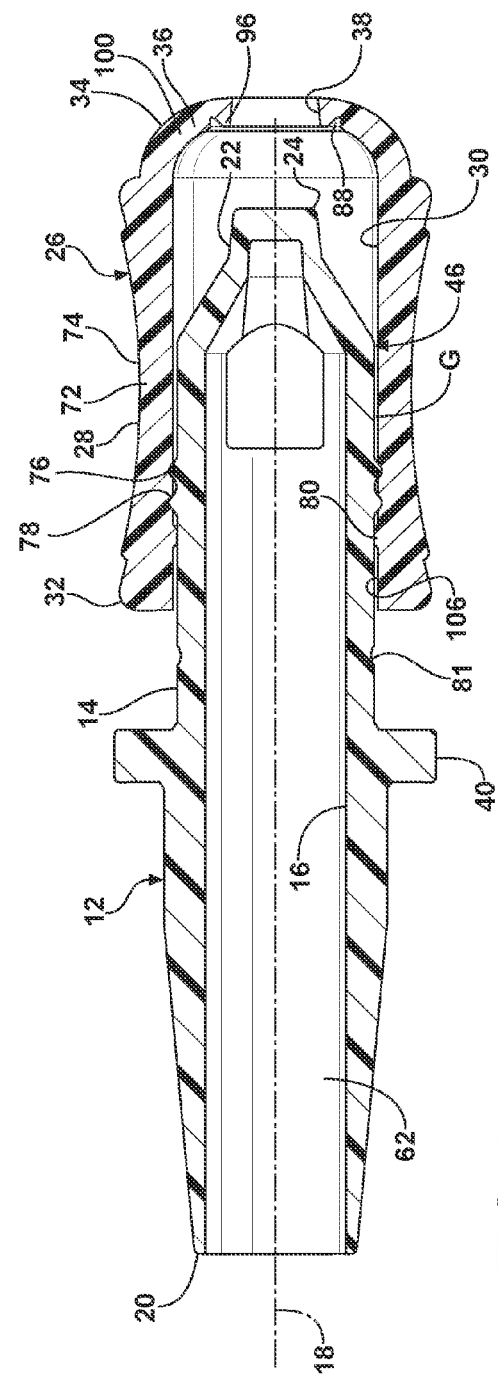

URINARY FLOW CONTROL VALVE WITH PRESSURE SEALING

FIELD OF THE INVENTION

The present invention relates generally to a valve for controlling fluid flow through a passage and, more particularly, to a manually operated slide valve providing improved operation and sealing between a valve cap member and a valve body.

BACKGROUND OF THE INVENTION

In medical liquid collection and fluid flow control systems, such as systems used to collect and/or control drainage of urine from a person's bladder, a valve is typically provided to control flow of fluid from the system. Such collection and control systems generally include a catheter having an end received in the bladder of the person, and a drainage tube connected to an opposing end of the catheter. Generally, prior art systems further include a collection bag connected to the downstream end of the drainage tube, wherein urine drains from the bladder through the catheter and drainage tube into the collection bag for retention therein. The collection bag is typically strapped to one of the person's legs or to a bedside and must be periodically drained as it fills.

In addition, a valve may be attached directly to a catheter or drainage tube to control flow of fluid through the catheter. For example, a urinary valve for controlling flow of fluid through a catheter is disclosed in U.S. Pat. No. 6,913,244. Disclosed herein is an improvement to such valves.

SUMMARY OF THE INVENTION

In accordance with an aspect of the invention, a valve is provided for controlling fluid flow through a flow passage. The valve comprises a tubular valve body comprising an interior surface and an exterior surface wherein the valve body defines a central longitudinal axis and first and second ends. A tip portion is supported on the valve body and is located at the second valve body end. A cap member is provided comprising an interior surface and an exterior surface, and is positioned over the second valve body end for movement in a longitudinal direction parallel to the longitudinal axis. The cap member includes an open end and a closed end. The closed end of the cap member comprises an end wall having a seal structure including a seal aperture for receiving the tip portion. The cap member is movable in a first direction toward the first valve body end to position the cap member in a closed position with the tip portion extending through the aperture to prevent fluid flow through the valve body, and the cap member is movable in a second direction away from the first valve body end to position the cap member in an open position with the aperture displaced from the tip portion to permit fluid flow through the valve body. The valve body is formed of a first substantially rigid material, and the cap member is formed of a second elastically flexible material, different from the first substantially rigid material, wherein the aperture is defined by an inner seal wall that conforms to an outer periphery of the tip portion.

In accordance with another aspect of the invention, a urinary valve is provided for controlling fluid flow through a flow passage. The valve comprises a tubular valve body comprising an interior surface and an exterior surface wherein the valve body defines a central longitudinal axis and first and second ends. A tip portion is supported on the valve body and is located at the second valve body end. A cap member is provided comprising an interior surface and an exterior surface, and is positioned over the second valve body end for movement in a longitudinal direction parallel to the longitudinal axis. The cap member includes an open end and a closed end. The closed end of the cap member comprises an end wall having a seal structure including a seal aperture for receiving the tip portion. The cap member is movable in a first direction toward the first valve body end to position the cap member in a closed position with the tip portion extending through the aperture to prevent fluid flow through the valve body, and the cap member is movable in a second direction away from the first valve body end to position the cap member in an open position with the aperture displaced from the tip portion to permit fluid flow through the valve body. The valve body is formed of a first material having a first hardness. The cap member is formed of a second material having a second hardness less than the first hardness, wherein the aperture is defined by an inner seal wall that conforms to an outer periphery of the tip portion. A lip portion is formed on the end wall of the cap member adjacent to the seal aperture and comprises an axially inner portion of the inner seal wall. A groove circumferentially surrounds the lip portion, and the groove includes a radially outer first groove wall and a radially inner second groove wall. Fluid pressure against the second groove wall, around the circumference of the groove, by fluid passing through the valve body effects a uniform application of radial pressure to the lip portion, when the cap member is in the closed position, preventing entry and/or accumulation of fluid in the area of contact between the tip portion and the inner seal wall.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 8 is a cross-sectional view through the valve of FIG. 1, illustrating the valve in a closed position; and FIG. 9 is a cross-sectional view through the valve of FIG. 1, illustrating the valve in an open position.

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
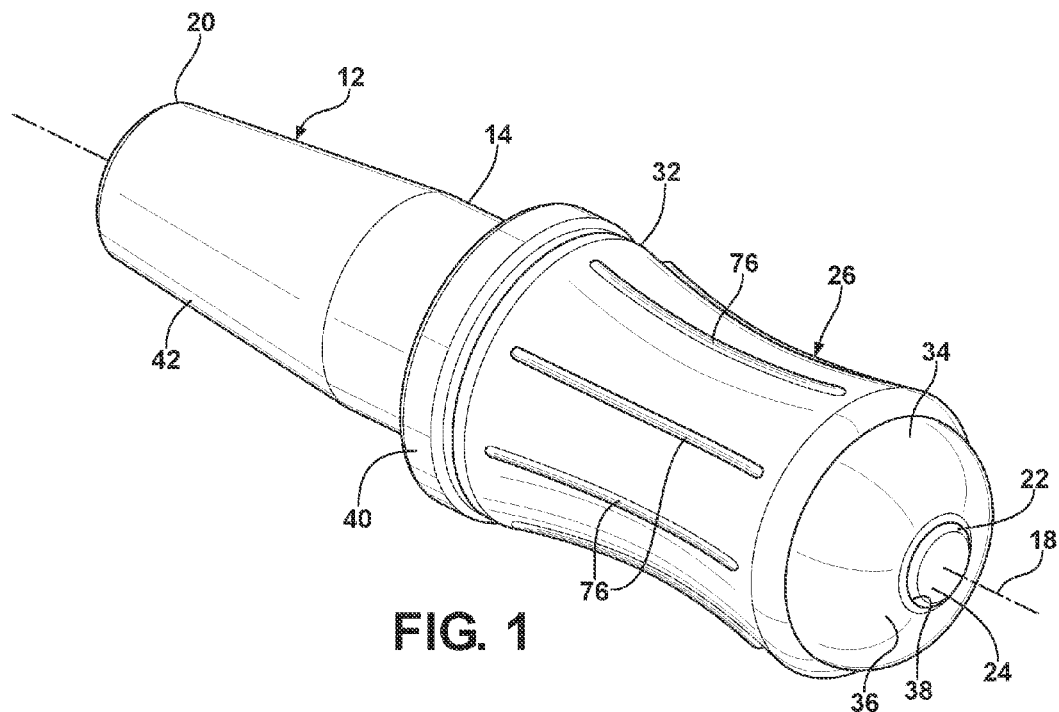
FIG. 1 is a perspective view of an embodiment of a valve in accordance with the present invention.
Figure 2:
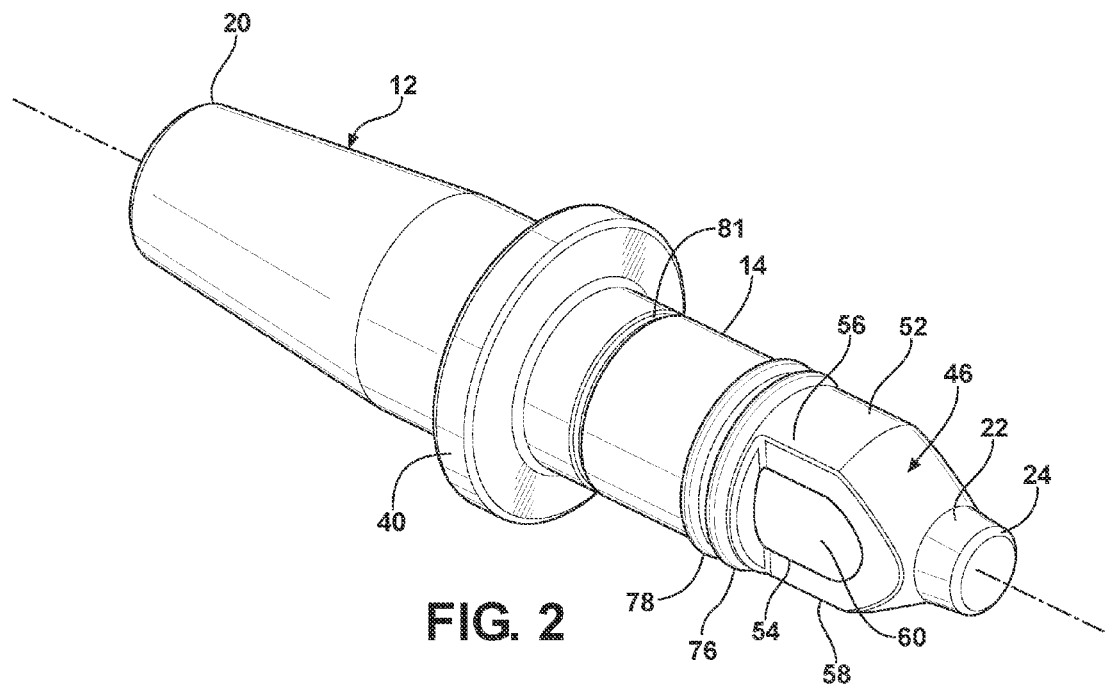
FIG. 2 is a perspective view of an embodiment of a valve body for the valve of FIG. 1.

Referring to FIG. 1, an embodiment of the present invention is illustrated including a valve 10 for controlling fluid flow through a flow passage and, in particular, may comprise a urinary valve for positioning in a flow passage defined by a urinary catheter (not shown) having an end located in a bladder as a source of fluid.

Referring additionally to FIGS. 8 and 9, the valve 10 generally includes a tubular valve body 12 comprising an interior surface 14 and an exterior surface 16. The valve body 12 defines a central longitudinal axis 18, and a first valve body end 20 and a second valve body end 22. The valve 10 includes a tip portion 24 having a diameter smaller than a diameter of the valve body 12 and supported on the valve body 12 at the second valve body end 22. A cap member 26 is supported on the valve body 12 and comprises an interior surface 30 facing inwardly toward the exterior surface 14 of the valve body 12, and an exterior surface 28 for engagement by a person operating the valve, as is described further below.

The cap member 26 is positioned over the second valve body end 22 for movement in a longitudinal direction parallel to the longitudinal axis 18. The cap member 26 further includes an open end 32 and a closed end 34. The closed end 34 comprises an end wall 36 having a seal structure including a seal aperture 38 having a diameter smaller than a diameter of the interior cap surface 30 and aligned along the longitudinal axis 18 for receiving the tip portion 24. The cap member 26 is movable in a first longitudinal direction toward the first valve body end 20 to position the cap member 26 in a closed position with the tip portion 24 extending through the seal aperture 38 to prevent fluid flow through the valve body 12 (FIG. 8), as is described in greater detail below. The cap member 26 is further movable in a second longitudinal direction away from the first valve body end 20 to position the cap member 26 in an open position with the seal aperture 38 displaced from the tip portion 24 to permit fluid flow through the valve body 12 (FIG. 9).

Referring to FIGS. 2-5, the valve body 12 is illustrated in greater detail and is shown as being configured as an elongated structure from the first valve body end 20 to the second valve body end 22, and defining the central longitudinal axis 18. The valve body 12 is preferably formed of a substantially rigid material such as medical grade polypropylene, having a hardness of Rockwell 65 R-scale. The first valve body end 20 comprises a fluid inlet for the valve body 12, and the second valve body end 22 comprises a fluid outlet for the valve body 12. The interior surface 16 of the valve body 12 defines a substantially constant interior diameter extending from the first valve body end 20 to a location adjacent to the second valve body end 22 for conducting fluid flow through the valve 10.

A flange 40 extends radially outwardly from the exterior surface 14 of the valve body 12 at a location approximately midway between the first and second valve body ends 20, 22. The exterior surface 14 of the valve body 12 is tapered at an angle over a tapered portion 42 extending from the first valve body end 20 toward the flange 40 whereby the diameter of the exterior surface 14 increases proceeding from the first valve body end 20 toward the second valve body end 22. The tapered portion 42 is adapted to be inserted into a tube such as a urinary catheter or drainage tube (not shown). The tapered portion 42 provides a progressively varying diameter which facilitates attachment of the valve 10 to tubes of different interior diameters. For example, the tapered portion 42 may comprise an angle of approximately 10°, as measured between diametrically opposing exterior portions of the exterior surface 14 of the tapered portion 42.

The exterior surface 14 of the valve body 10 includes a substantially constant diameter cylindrical portion 44 extending from the flange 40 toward the second valve end 22. A transition portion 46 is located at an end of the cylindrical portion 44. The transition portion 46 comprises a first portion 48, extending from and generally parallel to the cylindrical portion 44, and a second portion 50 that angles radially inwardly from the first portion 48 extending in a direction toward the second valve end 22. In particular, the first portion 48 comprises a pair of substantially linear legs 52, 54 extending parallel the longitudinal axis 18 and having respective curved outer walls 56, 58 with a radius of curvature substantially the same as the radius of curvature of the exterior surface 14 of the valve body 12. A through opening 60 is defined between the pair of legs 52, 54. The through opening 60 is open to a flow passage 62 (FIG. 5) defined by the interior surface 16 of the valve body 12, such that fluid flowing into the valve body 12 through the first end 20 may flow out of the valve body 12 through the through opening 60.

The second portion 50 comprises first and second substantially linear opposing sections 64, 66 extending from the pair of legs 52, 54 in converging relationship toward the second valve body end 22. The first and second sections 64, 66 may converge toward each other at an angle of approximately 60°, as measured between the opposing sections 64, 66. The first and second portions 48, 50 define opposing generally planar sides 68, 70 that are spaced apart a distance less than a diameter of the exterior surface 14 of the cylindrical portion 44.

The tip portion 24 is supported at the second valve end 22 on the transition portion 46 aligned with the central longitudinal axis 18 and defining a generally cylindrical end portion that preferably tapers slightly toward the axial outer end of the tip portion 24, such as at an angle of approximately 10°. In addition, the outer end of the tip portion 24 is preferably formed with a chamfer to facilitate smooth engagement with the aperture 38 of the cap member 26.

Figure 6:
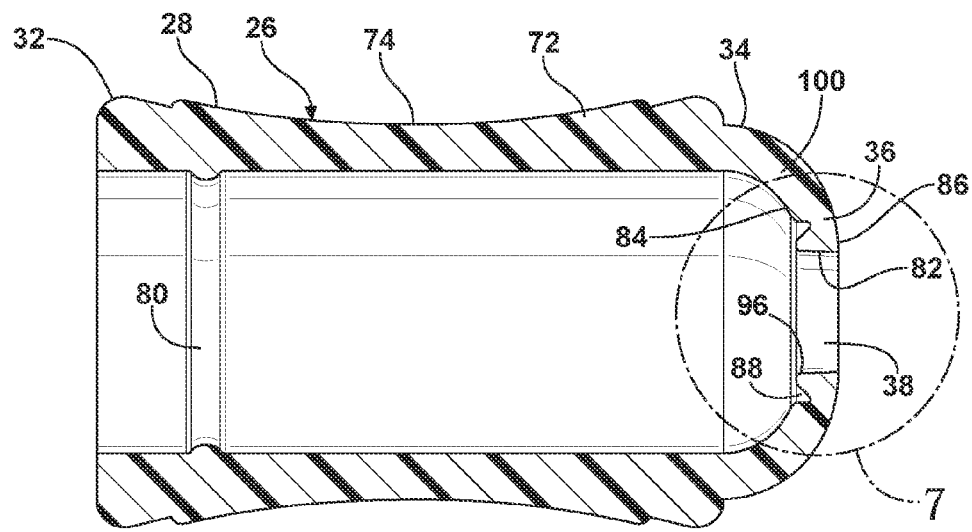
FIG. 6 is a cross-sectional view through a cap member shown on the valve in FIG. 1.

Referring to FIG. 6, the cap member 26 comprises a generally cylindrical body 72 extending from the open end 32 to the closed end 34. The cap member 26 is preferably formed of a relatively flexible material, having elastic properties for purposes that will be apparent below. In particular, the material of the cap member 26 may comprise a thermoplastic elastomer (TPE) having a hardness in the range of about 85 to 95 durometer Shore A, and preferably a hardness of about 90 durometer Shore A, such as a material comprising medical grade SANTOPRENE (SANTOPRENE is a registered trademark of Monsanto Company of St. Louis, Mo.) having the described hardness characteristic.

The interior cap member surface 30 comprises a substantially cylindrical surface defining small gap G (FIGS. 8 and 9), i.e., approximately 0.003 inch, between the exterior surface 14 of the valve body 12 and the interior surface 30 of the cap member 26. The exterior surface 28 of the cap member 26 defines an inwardly radiused outer wall 74 extending along substantially an entire length of the cap member 26, i.e., along the cylindrical body 72 of the cap member 26 from a location adjacent to the open end 32 to a location adjacent to the end wall 36 at the closed end 34, to define a saddle shaped outer wall 74. A plurality of longitudinally extending ribs 76 (FIG. 1) are located in circumferentially spaced relation to each other around the circumference of the saddle shaped outer wall 74. The saddle shaped outer wall 74 provides an engagement surface for engagement with a user's thumb and one or more fingers in effecting longitudinal and rotational movement of the cap member 26 relative to the valve body 12, for movement of the cap member 26 between the closed and open positions illustrated in FIGS. 8 and 9. The relatively more flexible, i.e., softer, material provides a greater tactile feel that may enable a user's fingers to engage and manipulate the cap member 26 relative the valve body 12, such as in manipulating the cap member 26 to an open or closed position in a single handed operation of the valve 10.

Figure 3:
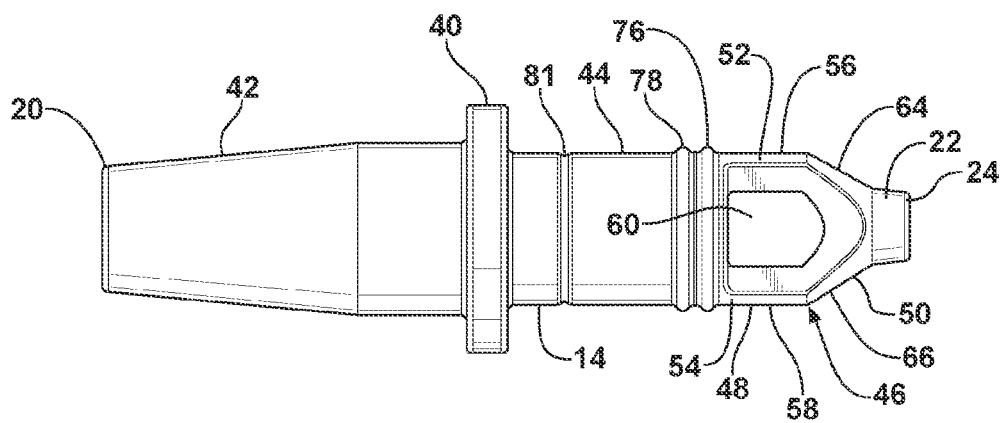
FIG. 3 is a side elevational view of the valve body of FIG. 2.
Figure 4:
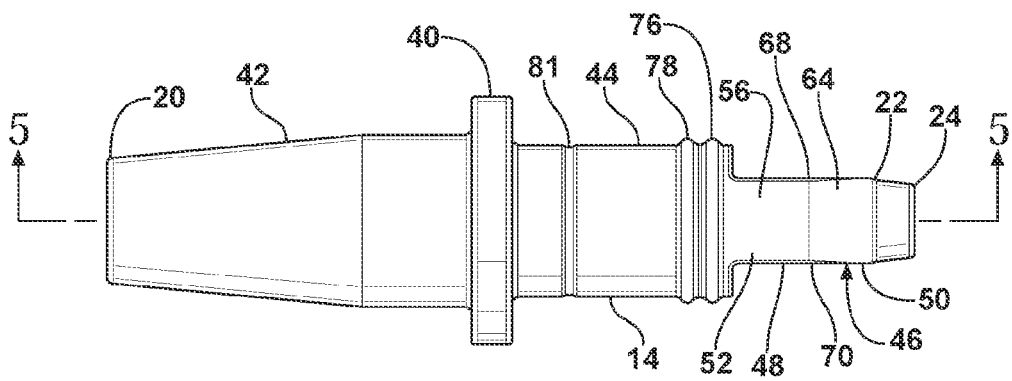
FIG. 4 is a top plan view of the valve body of FIG. 2.
Figure 5:
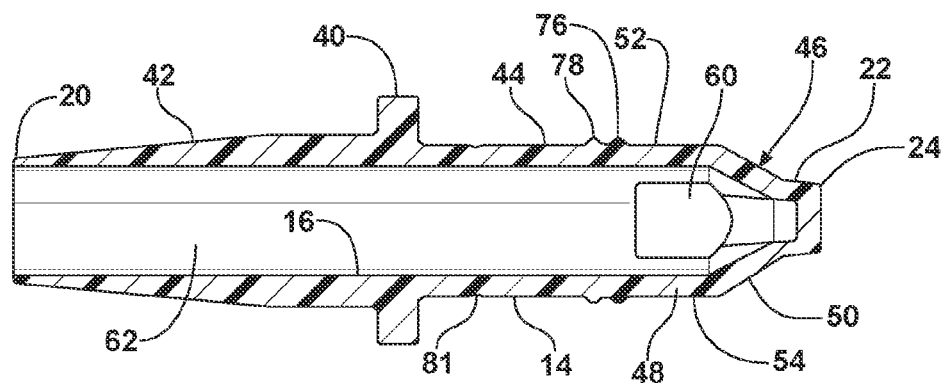
FIG. 5 is a cross-sectional view along line 5-5 in FIG. 4.

As may be best seen in FIGS. 3-5, the exterior surface 14 of the valve body cylindrical portion 44 is preferably formed with a dual seal structure comprising a pair of closely adjacent seal ribs 76, 78 for engagement with the interior surface 30 of the cap member 26. The seal ribs 76, 78 define an outer diameter that is larger than the diameter of the interior surface 30 of the cap member 26. For example, the outer diameter defined by the seal ribs 76, 78 may be approximately 0.009 inch larger than the interior diameter of the cap member 26. The pair of seal ribs 76, 78 are located directly adjacent to the first portion 48 of the transition portion 46 and form a seal with the cap member 26 to prevent fluid exiting the through passage 60 from traveling along the gap G past the ribs 76, 78 toward the open end 32 of the cap member 26. In particular, the dual seal structure is provided such that, if a manufacturing imperfection should occur in formation of one of the ribs 76, 78, the other of the ribs 76, 78 may operate to create the necessary circumferential seal with the interior surface 30 of the cap member 26 to prevent fluid flow through the gap G toward the first cap member end 32. That is, if one of the ribs 76, 78 has a manufacturing flaw, the other of the ribs 76, 78 is not likely to also have a flaw, and would ensure sealing at the interface between the ribs 76, 78 and the cap member 26.

Referring to FIG. 6, the cap member 26 is formed with a stop rib 80 extending radially inwardly from the interior surface 30 adjacent to the open end 32 of the cap member 26. The stop rib 80 is located to engage the seal rib 78 when the cap member 26 is in a fully open position relative to the valve body 12, see FIG. 9, and thereby define a limit position for longitudinal movement of the cap member 26 toward the open position. Further, the valve body 12 is formed with a groove 81 (FIGS. 3-5) for receiving the stop rib 80. The groove 81 extends circumferentially around an end of the cylindrical portion 44 adjacent to the flange 40 and is located to receive the stop rib 80 when the cap member 26 is retracted to position the open end 32 adjacent to the flange 40 in the closed position of the valve 10, see FIG. 8. An inner diameter defined by the stop rib 80 may be slightly smaller than the outer diameter defined by the exterior surface of the cylindrical portion 44 of the valve body 12. For example, the inner diameter of the stop rib 80 may be approximately 0.001 inch smaller than the outer diameter of the cylindrical portion 44.

It should be noted that the pair of seal ribs 76, 78 cooperating with the interior surface 30 of the cap member 26, and the stop seal 80 cooperating with the exterior surface 14 of the valve body cylindrical portion 44, operate to maintain the gap G as a small gap between the interior surface 30 of the cap member 26 and the exterior surface 14 of the cylindrical portion 44 of the valve body 12, while maintaining the cap member 26 aligned generally parallel to the central longitudinal axis 18 during longitudinal movement of the cap member 26. Accordingly, the contact areas between the cap member 26 and the valve body 12 are minimized to reduce the frictional forces resisting movement of the cap member 26 relative to the valve body 12, while providing for guided movement of the cap member 26 between the open and closed positions. Also, it should be noted that the spacing between the interior cap member surface 30 and the exterior surface 14 of the valve body 12 is very small, i.e., on the order of 0.015 inch, which may minimize any available space for fluid accumulation.

Figure 7:
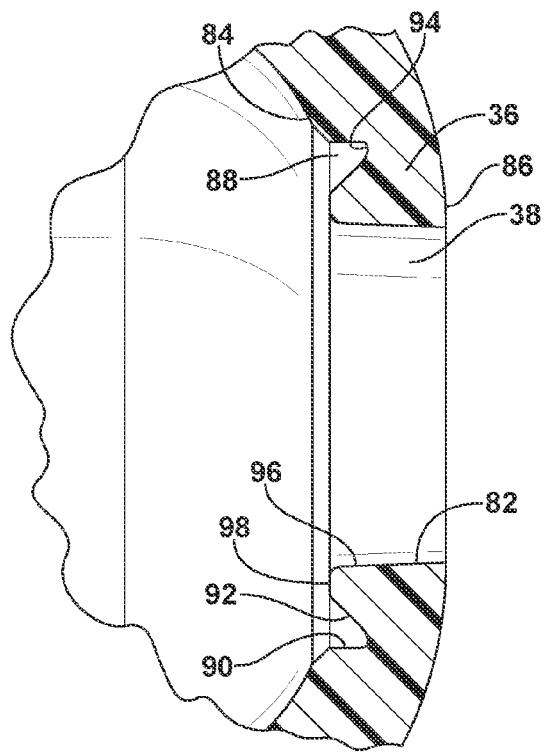
FIG. 7 is an enlarged detail view of an area identified in FIG. 6.

Referring to FIGS. 6 and 7, the aperture 38 is defined by an inner seal wall 82 wherein the relatively flexible material of the cap member 26, i.e., thermoplastic elastomer (SANTOPRENE), facilitates conforming of the inner seal wall 82 to an outer periphery of the tip portion 24 with a low compression set engagement between the inner seal wall 82 and the tip portion 24. The end wall 36 of the cap member 26 includes an end wall interior surface 84 facing axially toward the open end 32 of the cap member 26. The inner seal wall 82 tapers inwardly in direction from the end wall interior surface 84 toward an outer end surface 86 at an angle substantially similar to the taper angle of the tip portion 24, i.e., approximately 10°. Moreover, the diameter of the aperture 38 at the end wall interior surface 84 is slightly greater than the diameter of the end of the tip portion 24, i.e., greater by approximately 0.003 inch, facilitating initial passage of the tip portion 24 through the aperture 38 as the valve 10 is closed. Further, the diameter of the aperture 38 at the outer end surface 86 is slightly smaller than the diameter of the end of the tip portion 24, i.e., smaller by approximately 0.006 inch, such that a sealing interference fit is created between the tip portion 24 and the aperture 38 when the cap member 26 is in the closed position.

As best seen in FIG. 7, a circumferentially extending groove 88 is defined by first and second groove walls 90, 92 extending into the end wall interior surface 84, i.e., extending from the end wall interior surface 84 toward the outer end surface 86. The first groove wall 90 comprises a radially outer wall of the groove 88 and extends generally parallel to the longitudinal axis 18 of the valve body 12 from the end wall interior surface 84 to a groove base 94. The second groove wall 92 comprises a radially inner wall of the groove 88. The second groove wall 92 angles radially inwardly in a direction extending from a vertex junction with the first groove wall 90 at the groove base 94 to the end wall interior surface 84. An axially extending continuous annular lip portion 96 is formed between the inner seal wall 82 and the second groove wall 92 wherein a lip portion vertex 98 is defined at a junction between the inner seal wall 82 and the second groove wall 92. The lip portion 96 defines a generally V-shaped cross-section, and is pivotally movable radially relative to a portion of the end wall 84 surrounding the groove 88, i.e., radially inwardly in a direction toward the aperture 38. It should be noted that the resilient character of the material of the cap member 26 facilitates the pivotal or biased positioning of the inner seal wall 82 in response to fluid pressure at the groove 88. Fluid pressure against the second groove wall 92, as applied around the circumference of the groove 88, by fluid passing through the valve body 12 and out the through passage 60, may effect a substantially uniform application of radial pressure to the lip portion 96 when the cap member 26 is in the closed position. In particular, fluid pressure within the interior of the cap member 26 may facilitate sealing of the closed valve 10 in that the fluid pressure operates to increase the pressure of the inner seal wall 82 on the tip portion 24, with increasing fluid pressure facilitating sealing of the valve 10 by increasing the pressure of the inner seal wall 82 against the tip portion 24. It should further be noted that in addition to the close fit provided by the taper of the tip portion 24, the fluid pressure created sealing at the axially inner portion of the inner seal wall 82, as provided by the lip portion 96, may close any gaps or voids in the seal location to prevent fluid accumulation, i.e., to prevent entry of fluid, that might otherwise provide a potential location for growth of harmful organisms, such as bacteria.

Referring to FIG. 6, the closed end of the cap member 26 includes a connecting portion 100 comprising a radiused portion extending between the cylindrical cap body 72 and the end wall 36 to define a generally dome shaped area at the closed end 34. Referring to FIG. 8, along a substantial portion of the dome shaped area defined along the connecting portion 100, the interior surface 30 of the cap member 26 diverges from the transition portion 46 of the valve body 12. Further, the interior surface 30 of the cap member 26 at the closed end 34 is located at a radial distance 102 that is greater than the radial dimension of the gap G between the cap member 26 and the valve body 12. That is, the radial distance 102 has a minimum dimension, along the connecting portion 100 and adjacent portions of the cylindrical cap body 72 and end wall 36, that is greater than the dimension of the gap G, when the cap member 26 is located in the closed position, and defines an annular pressure chamber 104 adjacent to the groove 88 for receiving fluid from the through passage 60. The annular pressure chamber 104 provides a substantially even distribution of fluid around the circumference of the cap member closed end 34 and effects a substantially uniform pressure distribution of fluid pressure against the second wall 92 of the groove 88.

As the cap member 26 is moved along the valve 10 in the direction toward the flange 40, the tip portion 24 enters the seal aperture 38, engaging the inner seal wall 82. In the closed position, the tip portion 24 may extend slightly past the exterior outer end surface 86 defined at the end wall 36. Hence, the valve seal defined between the tip portion 24 and the end wall 36 is located at or adjacent to an exposed location, where the cooperating surfaces may be accessible to a user. Further, the outwardly extending shape provided to both the tip portion 24 and the exterior of the cap member end wall 36 is such that substantially any portion of the surfaces of the tip portion 24 and end wall 36 exposed to the atmosphere will be accessible for wiping and cleaning after the valve 10 is closed following use. Such a cleaning operation may be performed using an isopropyl alcohol pad or using mild soap and water to wipe the exposed surfaces clean. It may also be noted that the seal configuration provided by the current configuration avoids accumulation of fluid at the seal location which, in combination with wipable exterior surfaces, substantially avoids growth of organisms that may induce infections, e.g., urinary infections, in a person using the valve 10.

The use of a TPE material, such as SANTOPRENE, for the cap member 26 provides a reduced frictional force between the cap member 26 and the valve body 12. Further, a silicone lubricant 106 (FIGS. 8 and 9), e.g., silicone oil, is preferably provided at the contact areas between the cap member 26 and the valve body 12 to facilitate smooth movement of the cap member 26 relative to the valve body 12. The silicone will not absorb into polypropylene (valve body 12) or TPE (cap member 26), such that use of these materials may enable extended lubrication of the cap member 26 to facilitate use of the valve 10.

The relatively softer material of the cap member 26 provides a substantially resilient shielding function to the closed end 34 of the valve 10 wherein, in an application where the valve 10 is located at the end of a catheter or drainage tube, the cap member 26 will act as a cushion against a user if, for example, the user should position the valve 10 between a hard surface, e.g., a seat, and the user's leg. Hence, the present valve 10, incorporating the relatively softer TPE cap member 26, in combination with smooth edges and/or dome shaped surfaces, advantageously provides a cushioning effect to the valve 10 without effecting a distortion of the cap member 26 sealing areas, such that the cap member 26 maintains a fluid seal in the closed position.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A urinary valve for controlling fluid flow through a flow passage comprising:
   a tubular valve body comprising an interior surface and an exterior surface, the valve body defining a central longitudinal axis and first and second ends;
   a tip portion supported on the valve body and located at the second valve body end;
   a cap member comprising an interior surface and an exterior surface and positioned over the second valve body end for movement in a longitudinal direction parallel to the longitudinal axis;
   the cap member including an open and a closed end, the closed end comprising an end wall having a seal structure including a seal aperture for receiving the tip portion;
   the cap member being movable in a first direction toward the first valve body end to position the cap member in a closed position with the tip portion extending through the aperture to prevent fluid flow through the valve body, and the cap member being movable in a second direction away from the first valve body end to position the cap member in an open position with the aperture displaced from the tip portion to permit fluid flow through the valve body;
   the valve body being formed of a first substantially rigid material; and
   the cap member being formed of a second elastically flexible material, different from and softer than the first substantially rigid material, wherein the aperture is defined by an inner seal wall that conforms to an outer periphery of the tip portion to effect a low compression set engagement between the inner seal wall and the tip portion;
   a lip portion formed on the end wall of the cap member adjacent to the seal aperture and comprising an axially inner portion of the inner seal wall;
   wherein the end wall of the cap member includes an end wall interior surface facing axially toward the open end of the cap member, and the cap member further comprising:
      a circumferentially extending groove defined by first and second groove walls, each groove wall extending axially into the end wall interior surface;
      the first groove wall comprising a radially outer wall of the groove and extending generally parallel to the longitudinal axis of the valve body from the end wall interior surface to a groove base;
      the second groove wall comprising a radially inner wall of the groove, the second groove wall angling radially inwardly from a vertex junction with the first groove wall at the groove base to the end wall interior surface, and the second groove wall forming a lip portion vertex at a junction with the inner seal wall.

2. The urinary valve of claim 1, wherein the material of the valve body has a hardness of greater than about Rockwell 65 R-scale, and the material of the cap member has a hardness in the range of about 85 to about 95 durometer Shore A to effect the low compression set engagement between the inner seal wall and the tip portion.

3. The urinary valve of claim 2, wherein the valve body is formed of polypropylene and the cap member is formed of a thermoplastic elastomer (TPE).

4. The urinary valve of claim 3, wherein the TPE comprises medical grade SANTOPRENE having a hardness of about 90 durometer Shore A.

5. The urinary valve of claim 3, including a silicone oil at an interface between the valve body and the cap member.

6. The urinary valve of claim 1, wherein the lip portion defines a generally V-shaped cross-section, and is pivotally movable radially relative to a portion of the end wall surrounding the groove.

7. The urinary valve of claim 1, wherein:
the exterior surface of the valve body comprises a generally cylindrical portion and a transition portion extending between the cylindrical portion and the tip portion, the transition portion comprising at least two substantially linear opposing sections extending in converging relationship in a direction from the first valve body end toward the second valve body end; and
the cap member including a generally cylindrical portion and a connecting portion extending between the cylindrical portion of the cap member and the end wall, the cylindrical portion of the cap member and at least a portion of the connecting portion defining a surface that diverges from the opposing sides of the tapered portion to form an annular pressure chamber surrounding and in fluid communication with the groove to provide a substantially uniform fluid pressure against the second groove wall around the circumference of the groove by fluid passing through the valve body, and thereby effect a uniform application of pressure to the lip portion, when the cap member is in the closed position.

8. The urinary valve of claim 1, wherein the interior surface of the cap member comprises a generally cylindrical portion defining an interior diameter for cooperating with the exterior surface of the valve body and the interior diameter of the cap member and the interior diameter of the cap member interior surface is greater than a diameter defined by the inner seal wall, and the inner seal wall defines a diameter that is smaller than a diameter defined by the tip portion for engaging the inner seal wall in the closed position, such that the inner seal wall elastically conforms to the shape of the tip portion to effect a fluid seal in the closed position.

9. The urinary valve of claim 8, wherein the cap member comprises a hardness in the range of about 85 to about 95 durometer Shore A to effect the low compression set engagement between the inner seal wall and the tip portion.

10. The urinary valve of claim 9, including at least one seal rib formed on and extending circumferentially around the exterior surface of the valve body for engaging the interior surface of the cap member, wherein a radially outer diameter of the at least one seal rib is greater than the interior diameter of the cap member, to form a low compression set interference fit between the cap member and the valve body.

11. A urinary valve for controlling fluid flow through a flow passage comprising:

a tubular valve body comprising an interior surface and an exterior surface, the valve body defining a central longitudinal axis and first and second ends;
a tip portion supported on the valve body and located at the second valve body end;
a cap member comprising an interior surface and an exterior surface and positioned over the second valve body end for movement in a longitudinal direction parallel to the longitudinal axis;
the cap member including an open and a closed end, the closed end comprising an end wall having a seal structure including a seal aperture for receiving the tip portion;
the cap member being movable in a first direction toward the first valve body end to position the cap member in a closed position with the tip portion extending through the aperture to prevent fluid flow through the valve body, and the cap member being movable in a second direction away from the first valve body end to position the cap member in an open position with the aperture displaced from the tip portion to permit fluid flow through the valve body;
the valve body being formed of a first substantially rigid material; and
the cap member being formed of a second elastically flexible material, different from the first substantially rigid material, wherein the aperture is defined by an inner seal wall that conforms to an outer periphery of the tip portion;
a lip portion formed on the end wall of the cap member adjacent to the seal aperture and comprising an axially inner portion of the inner seal wall;
wherein the end wall of the cap member includes an end wall interior surface facing axially toward the open end of the cap member, and the cap member further comprising:
a circumferentially extending groove defined by first and second groove walls extending walls, each groove wall extending axially into the end wall interior surface;
the first groove wall comprising a radially outer wall of the groove and extending generally parallel to the longitudinal axis of the valve body from the end wall interior surface to a groove base;
the second groove wall comprising a radially inner wall of the groove, the second groove wall angling radially inwardly from a vertex junction with the first groove wall at the groove base to the end wall interior surface, and the second groove wall forming a lip portion vertex at a junction with the inner seal wall; and
the lip portion further defines a generally V-shaped cross-section, and is pivotally movable radially relative to a portion of the end wall surrounding the groove.

* * * * *

UNITED STATES PATENT AND TRADEMARK OFFICE
CERTIFICATE OF CORRECTION

PATENT NO. : 8,512,313 B2
APPLICATION NO. : 12/611184
DATED : August 20, 2013
INVENTOR(S) : Gordon Edgar Atkinson et al.

It is certified that error appears in the above-identified patent and that said Letters Patent is hereby corrected as shown below:

In the Spec.:

Col. 5, lines 52-53, "maintain the gap Gas a small gap" should read --maintain the gap G as a small gap--.

Signed and Sealed this
Twelfth Day of November, 2013

Teresa Stanek Rea
*Deputy Director of the United States Patent and Trademark Office*